United States Patent [19]

Yokomori et al.

[11] Patent Number: 5,565,212
[45] Date of Patent: Oct. 15, 1996

[54] PROCESS FOR PRODUCING COMPOSITIONS FOR RUMINANTS

[75] Inventors: Yorozu Yokomori; Toshikazu Murayama, both of Yokkaichi; Tomoaki Masada, Mishima; Motohiro Ohta, Shizuoka-ken; Masaki Azuma; Yoshio Yumiba, both of Hofu, all of Japan

[73] Assignee: Kyowa Hakko Kogyo Co., Ltd., Tokyo, Japan

[21] Appl. No.: 405,458

[22] Filed: Mar. 16, 1995

Related U.S. Application Data

[63] Continuation of Ser. No. 118,758, Sep. 10, 1993, abandoned.

[30] Foreign Application Priority Data

Sep. 11, 1992 [JP] Japan ................... 4-243157

[51] Int. Cl.$^6$ ................................ A23K 1/18
[52] U.S. Cl. ........................... 424/438; 424/489
[58] Field of Search ................... 424/438, 489

[56] References Cited

U.S. PATENT DOCUMENTS

| | | | |
|---|---|---|---|
| 4,234,565 | 11/1980 | Flodin | 424/33 |
| 4,837,004 | 6/1989 | Wu | 424/438 |
| 4,877,621 | 10/1989 | Ardaillon | 424/498 |
| 4,996,067 | 2/1991 | Kobayashi | 426/96 |
| 5,080,917 | 1/1992 | Itoh et al. | 426/96 |
| 5,225,238 | 7/1993 | Ardaillon | 427/3 |
| 5,244,669 | 9/1993 | Satoh | 424/438 |

FOREIGN PATENT DOCUMENTS

| | | |
|---|---|---|
| 447298 | 9/1991 | European Pat. Off. |
| 88844/86 | 10/1984 | Japan |
| 88843/86 | 10/1984 | Japan |
| 8000659 | 4/1980 | WIPO |

*Primary Examiner*—D. Gabrielle Phelan
*Attorney, Agent, or Firm*—Antonelli, Terry, Stout & Kraus

[57] ABSTRACT

Disclosed is a process for producing a composition for ruminants, which is characterized in that a nucleus containing a physiologically active substance is coated with a coating material prepared by suspending in water (i) an emulsion comprising water and at least one hydrophobic substance hardly soluble in water and (ii) a slurry containing at least one polymer soluble in water of pH 5.0 or below and insoluble in water of pH over 5.0 In the process, an aqueous suspension is used for coating instead of a meterial dissolved in an organic solvent.

1 Claim, No Drawings

PROCESS FOR PRODUCING COMPOSITIONS FOR RUMINANTS

This application is a continuation of Ser. No. 08/118,758, filed Sept. 10, 1993, now abandoned.

BACKGROUND OF THE INVENTION

The present invention relates to a novel process for producing compositions for ruminants in which an aqueous suspension is used for coating.

In ruminants, substances orally administered are stored in the rumen of pH 5.5 and then absorbed into a blood stream in the abomasum of pH 3.0.

In order to increase the absorption of physiologically active substances in the abomasum, there have been developed compositions for ruminants utilizing coating materials which have a suppressive effect on the decomposition of the active substances in the rumen, but do not have a suppressive effect on the absorption of the active substances in the abomasum.

For example, Japanese Published Unexamined Patent Application Nos. 88843/86, 88844/86 and U.S. Pat No. 5,080,917 (EP-A-336,713) disclose compositions which comprise as a coating a hydrophobic substance hardly soluble in water of pH 5.5 or above and a polymer soluble in water of pH 5.0 or below. The compositions are produced by coating a granulated physiologically active substance as a nucleus with a coating material by spraying. The coating material is prepared by dissolving a hydrophobic substance hardly soluble in water of pH 5.5 or above and a polymer soluble in water of pH 5.0 or below in an organic solvent. During the spray coating, a large quantity of the organic solvent evaporates and diffuses into the air. Such process involves the danger of pollution and fire.

Therefore, it is desired to develop a process for producing compositions for ruminants which does not involve such problem.

SUMMARY OF THE INVENTION

The present invention provides a process for producing a composition for ruminants which is characterized in that a nucleus containing a physiologically active substance is coated with a coating material prepared by suspending in water (i) a hydrophobic substance hardly soluble in water and (ii) a polymer soluble in water of pH 5.0 or below and insoluble in water of pH over 5.0.

DETAILED DESCRIPTION OF THE INVENTION

The coating material used in the present invention may be prepared by any method so long as it is an aqueous suspension of (i) a hydrophobic substance hardly soluble in water and (ii) a polymer soluble in water of pH 5.0 or below and insoluble in water of pH over 5.0.

For example, the coating material can be prepared by suspending in water (i) an emulsion comprising water and at least one hydrophobic substance hardly soluble in water and (ii) a slurry containing at least one polymer soluble in water of pH 5.0 or below and insoluble in water of pH over 5.0, if necessary, in the presence of a filler.

The emulsion comprising water and at least one hydrophobic substance hardly soluble in water can be prepared in the following manner. The hydrophobic substance is dissolved in an appropriate quantity of an organic solvent, together with an emulsifier, and then the resulting solution is dropped and dispersed in water, followed by the removal of the organic solvent with heating at 40° to 100° C. at ordinary pressure or under reduced pressure. It is preferable that the removed organic solvent is recovered by a cooler. Alternatively, the hydrophobic substance may be dissolved in an appropriate quantity of an organic solvent and then dropped and dispersed in water containing an emulsifier, followed by the removal of the organic solvent as described above.

Examples of the hydrophobic substances hardly soluble in water include saturated fatty acids containing not less than 14 carbon atoms and metal salts thereof, higher fatty alcohols containing not less than 12 carbon atoms, hardened animal and vegetable oils, and natural and synthetic polymers.

Examples of the saturated fatty acids containing not less than 14 carbon atoms include straight-chain or branched monocarboxylic acids such as myristic acid, palmitic acid and stearic acid, and examples of their metal salts include calcium, magnesium, barium and iron salts. Examples of the higher fatty alcohols containing not less than 12 carbon atoms include laurel alcohol, myristyl alcohol, cetyl alcohol and stearyl alcohol. Examples of the hardened animal and vegetable oils include hardened beef tallow oil and hardened castor oil. An example of the natural polymer is shellac. Examples of the synthetic polymers include copolymer resins of styrene, vinyl chloride, vinylidene chloride, acrylic esters, methacrylic esters, vinyl acetate and the like; resins such as polyesters, polyurethanes, nylons and polyacetals; and derivatives of natural polymers such as cellulose acetate, ethyl cellulose and propyl cellulose.

Examples of the organic solvents include toluene, xylene, acetone, methyl ethyl ketone, isobutyl ketone, ethyl acetate, butyl acetate and chloroform. The solvents are used in an amount of 140 to 700 wt % based on the weight of the hydrophobic substance contained in the solvents.

Examples of the emulsifiers include nonionic emulsifiers such as polyoxyethylene alkyl ethers, polyoxyethylene alkylphenol ethers, sorbitan fatty acid esters, polyoxyethylene sorbitan fatty acid esters, polyoxyethylene acyl esters, polyoxyethylene oxypropylene block copolymers and fatty acid monoglycerides; anionic emulsifiers such as salts of fatty acids, salts of sulfuric esters of higher alcohols, alkylbenzenesulfonate, alkylnaphthalenesulfonate, dialkylsulfosuccinate, salts of alkyl phosphate and salts of polyoxyethylene sulfate; and cationic emulsifiers such as salts of alkylamines, quaternary ammonium salts and polyoxyethylene alkylamines. The emulsifiers are used in an amount of 1 to 30 parts by weight, preferably 2 to 20 parts by weight, based on 100 parts by weight of the hydrophobic substance.

The hydrophobic substance may be contained in the emulsion in an amount of 1 to 50 wt % based on the weight of the entire emulsion.

In cases where the hydrophobic substance hardly soluble in water is a synthetic copolymer resin, it is possible to prepare the emulsion in accordance with a known method [Soichi MUROI "Chemistry of Copolymer Latex," published by Kobunshi Kankokai (1970)]. A commercially available emulsion, for example, Ethyl Cellulose Emulsion (produced by FMC Co.) can also be used as the emulsion comprising water and a hydrophobic substance hardly soluble in water.

Examples of the polymers soluble in water of pH 5.0 or below and insoluble in water of pH over 5.0 to be contained in the slurry include cellulose derivatives such as benzylaminomethyl cellulose, dimethylaminomethyl cellulose, piperidyiethyl hydroxyethyl cellulose, cellulose acetate dimethylaminoacetate, cellulose acetate diethylaminoacetate and cellulose acetate dibutylaminohydroxypropyl ethers; polyvinyl derivatives such as vinyldiethylamine-vinyl acetate copolymers, vinylbenzylamine-vinyl acetate copolymers, polyvinyldiethylaminoacetoacetals, vinylpiperidylacetoacetal-vinyl acetate copolymers, polyvinyl acetal diethylamino acetate, polydimethylaminoethyl methacrylate, polydiethylaminomethylstyrenes, polyvinylethylpyridines, vinylethylpyridine-styrene copolymers, vinylethylpyridine-acrylonitrile copolymers, methylvinylpyridine-acrylonitrile copolymers and methylvinylpyridine-styrene copolymers; copolymers of dimethylaminoethyl methacrylate and one or more acrylic acid alkyl esters and/or methacrylic acid alkyl esters; nitrogen-containing polysaccharides such as chitosan and chitin; and metal salts of polysaccharides such as calcium alginate. These polymers can be used either individually or in combination.

The slurry can be obtained by the following method. The polymer soluble in water of pH 5.0 or below and insoluble in water of pH over 5.0 is granulated to fine particles (diameter: 100 μm or less) by a jet mill, a ball mill, a colloid mill or the like. The fine particles are dispersed in water, preferably in the presence of an emulsifier as mentioned above and, if necessary, in the presence of a coagulation inhibitor such as talc. In order to obtain a stable slurry, it is preferred to add an emulsifier in an amount of 1 to 10 parts by weight, based on 100 parts by weight of the polymer. The polymer is contained in the slurry preferably at a concentration of 10 to 30% by weight. Commercially available polymers, for example, AEA (trademark for a polyvinylacetal diethylaminoacetate produced by Sankyo Co., Ltd.) and Eudragid E100 (trademark for a copolymer consisting of dimethylaminoethyl acrylate, a methacrylic acid alkyl ester and at least one acrylic acid alkyl ester produced by Rohm Pharm. Co.), can also be used as the polymer soluble in water of pH 5.0 or below and insoluble in water of pH over 5.0.

As the filler, there can be used inorganic substances such as talc, kaolin, mica, silica, calcium carbonate, diatomaceous earth and barium sulfate; metal salts (e.g., calcium, barium or iron salts) of water-insoluble fatty acids having at least 12 carbon atoms, such as palmitic acid, stearic acid and myristic acid; alcohols such as lauryl alcohol, myristyl alcohol and stearyl alcohol; and pulverized particles of hardened material of thermosetting polymers such as pulverized particles of hardened epoxy resin acid anhydrides and of hardened. These fillers can be used either individually or in combination.

Inorganic fillers are used preferably in the form of fine powders pulverized beforehand, and non-inorganic fillers are used preferably in the form of an aqueous slurry of fine particles pulverized beforehand to a size of 100 μm or less.

The hydrophobic substance hardly soluble in water (B), the polymer soluble in water of pH 5.0 or below and insoluble in water of pH over 5.0 (C) and the filler (D) are admixed at the following ratio:

$B/(C+D) = 100/10$ to $100/200$ $C/D = 100/2$ to $100/1000$ $B/C = 95/5$ to $20/80$, preferably 90/10 to 40/60 and the resulting mixture is suspended in water to prepare the coating material. The final volume of water is 1.5 to 18 times that of (B+C+D).

Examples of the physiologically active substances include amino acids such as methionine, lysine, tryptophan, threonine, glutamic acid, glutamine and aspartic acid; vitamins such as vitamin A; proteases such as acidic protease; saccharides such as glucose; antibiotics such as penicillin; and anthelmintics such as levamisole.

The nuclei containing a physiologically active substance can be produced by pelletizing a mixture of the physiologically active substance, an excipient, a binder and, if necessary, other ingredients (e.g., inorganic substance) by the use of an extrusion granulator, and then shaping the pellets into spheres by the use of a rounder.

Examples of the binders include cellulose derivatives such as methyl cellulose, ethyl cellulose, hydroxypropyl cellulose and hydroxypropyl methyl cellulose; vinyl derivatives such as polyvinyl alcohol and polyvinyl pyrrolidone; starch; fatty acids; hardened vegetable oils; and hardened animal oils. Examples of the excipients include starch and fine crystalline cellulose; and examples of the inorganic substances include calcium carbonate, calcium phosphate and talc.

It is preferred to produce the nuclei in the spherical or granular form. Though the size of the nuclei is not particularly limited, they are usually 0.1 to 10 mm in diameter.

Coating of the nuclei with the coating material can be carried out by spraying at a temperature of 40° to 120° C. The coating material is used in an amount of 5 to 50 parts by weight based on 100 parts by weight of the nuclei. Any usual coating method can be utilized for the coating, including the pan coating method, the fluidization coating method and the centrifugal fluidization coating method.

The compositions obtained as above can be used for feed additives, medicines, and the like for ruminants.

In the present invention, an organic solvent is used only in the preparation of the emulsion. The obtained emulsion containing the organic solvent is heated and the evaporated organic solvent is recovered. Thus the organic solvent does not diffuse into the air.

Furthermore, in the coating process of the present invention, as an aqueous suspension is used instead of the material dissolved in an organic solvent. The coating process of the present invention avoids the diffusion of an organic solvent into the air.

In conclusion, the process of the present invention is effective for the prevention of pollution and fire.

The nucleus of a composition for ruminants should dissolve only in the abomasum. The specificity of the site of dissolution of the nucleus depends on the coating of the nucleus in general, coating of the nucleus with an aqueous suspension has been considered to be unsuitable for getting the desired effect on the dissolution of the nucleus at the specific site.

The dissolution rate of the compositions obtained according to the process is shown below.

TEST EXAMPLE

Methionine Oral Administration Compositions 1 to 3 and Lysine Oral Administration Compositions 4 to 6 were prepared in accordance with the process of the present invention, and Methionine Oral Administration Composition (a) and Lysine Oral Administration Composition (b) were prepared according to a known method using an organic solvent (as shown in Reference Examples 1 and 2). The compositions were subjected to a dissolution test under the conditions set forth in Table 1.

TABLE 1

| Test Conditions | |
|---|---|
| Test Liquid: | pH = 3.0: (A model for abomasum) Primary potassium citrate - hydrochloric acid |
| | pH = 6.0: (A model for rumen) Primary potassium citrate - sodium hydroxide |
| Quantity of Liquid: | 500 ml |
| Liquid Temperature: | 37° C. |
| Sample (pills): | 500 mg |
| Detection Method: | Methionine: HPLC method Detected at Wavelength of 210 nm Column = Nucleocil C18 (by Nippon Gas Chromatography Kogyo Co., Ltd.) Lysine: Ninhydrin reaction OD method, 565 nm |
| Test Method: | Japanese Pharmacopoeia No. 11, General test method, Dissolution test, Paddle method, Number of rotation = 100 r.p.m. |

The rates of dissolution were measured at six points (0.5, 1, 2, 3, 4 and 5 hours from the beginning of the test). The rates of dissolution of the compositions at pH 3.0 and 6.0 are shown in Table 2.

TABLE 2

| Composition | | Dissolution rate of the nucleus (%) | | | | | |
|---|---|---|---|---|---|---|---|
| | | time from the beginning of the experiment | | | | | |
| sition | pH | 0.5 hr | 1.0 hr | 2.0 hrs | 3.0 hrs | 4.0 hrs | 5.0 hrs |
| 1 | 6.0 | 0 | 0 | 0 | 0 | 0 | 0 |
|   | 3.0 | 78 | 90 | 102 | 101 | 100 | 101 |
| 2 | 6.0 | 0 | 0 | 0 | 0 | 0 | 0 |
|   | 3.0 | 65 | 91 | 97 | 102 | 98 | 99 |
| 3 | 6.0 | 0 | 0 | 0 | 0 | 0 | 0 |
|   | 3.0 | 60 | 87 | 94 | 103 | 101 | 102 |
| 4 | 6.0 | 0 | 0 | 0 | 0 | 0 | 0 |
|   | 3.0 | 55 | 96 | 98 | 99 | 97 | 99 |
| 5 | 6.0 | 0 | 0 | 0 | 0 | 0 | 0 |
|   | 3.0 | 50 | 87 | 95 | 101 | 100 | 100 |
| 6 | 6.0 | 0 | 0 | 0 | 0 | 0 | 0 |
|   | 3.0 | 73 | 92 | 97 | 100 | 98 | 101 |
| (a) | 6.0 | 0 | 0 | 0 | 0 | 0 | 0 |
|   | 3.0 | 99 | 98 | 101 | 102 | 100 | 101 |
| (b) | 6.0 | 0 | 0 | 0 | 0 | 0 | 0 |
|   | 3.0 | 96 | 97 | 101 | 103 | 100 | 104 |

Table 2 shows that the compositions according to the present invention are not dissolved at pH 6.0 (rumen) and dissolved at pH 3.0 (abomasum). Though the nucleus is coated with an aqueous suspension, the present invention shows the desired effect on the dissolution of the nucleus at the specific site. Furthermore, Table 2 shows that the present invention has the same effect as the known method. That is, in spite of the general view, it is apparent that the use of an aqueous suspension for coating in the preparation of compositions for ruminants can give the same effect as given by the use of a meterial dissolved in an organic solvent.

Certain embodiments of the invention are illustrated in the following examples.

EXAMPLE 1

(1) Preparation of Methionine Granules

DL-Methionine (2,000 g) was mixed with 400 g of a 20% (w/w) aqueous solution of polyvinyl alcohol as a binder. The resulting mixture was extruded through a cylindrical granulating machine having a screen (diameter: 2.0 mm) and then shaped into spheres by using a Marumerizer (produced, by Fuji Powdal Co.). The resulting granules were sieved through a sieve of 8 to 10 mesh and then dried in a current of air at 60° C. for one hour to obtain granules of a diameter of 1.7 to 2.4 mm.

(2) Preparation of AEA Slurry

AEA (produced by Sankyo Co., Ltd.) was pulverized using a ball mill and sieved through a sieve of 200 mesh. The obtained AEA particles (290 g) was admixed and stirred with 10 g of polyoxyethylene lauryl ether (Emulgen 106; produced by Kao Corp.) and 700 g of water, and the resulting mixture was dispersed using a sand mill to obtain a slurry of AEA.

(3) Preparation of Polyvinyl Acetate Slurry

Polyvinyl acetate was pulverized using a ball mill under cooling and then sieved through a sieve of 200 mesh. In order to prevent consolidation, 10 parts by weight of talc was added to 100 parts by weight of the sieved polyvinyl acetate particles. Then, the resulting polyvinyl acetate particles (285 g) was admixed and stirred with Emulgen 106 (15 g) and water (700 g), and the resulting mixture was dispersed using a sand mill to obtain a slurry of polyvinyl acetate.

(4) Preparation of Methionine Oral Administration Composition 1

In 200 g of water were suspended 200 g of a commercially available ethyl cellulose emulsion [composition: water 70%, solids 30% (ethyl cellulose, 87%; cetyl alcohol, 9%; and lauryl sulfate, 4%); product of FMC Co.], the AEA slurry (80 g) and the polyvinyl acetate slurry (120 g), to obtain a coating liquid. By using a fluidized-bed apparatus, the methionine granules (1,000 g) were coated with the coating liquid (600 g) by spraying to obtain Methionine Oral Administration Composition 1.

EXAMPLE 2

(1) Preparation of Stearic Acid Emulsion

Stearic acid (200 g) and ammonium laurylsulfate (12 g) were dissolved in a mixture of toluene (200 g) and ethyl acetate (200 g). The solution was added dropwise to water (2 liters) with stirring, and the resulting dispersion was concentrated by removing the solvents at 80° C. under reduced pressure (50 torr.) to obtain a stearic acid emulsion having a solid content of 30%.

(2) Preparation of Eudragid E100 Slurry

A slurry of Eudragid E100 was prepared according to the same method as in the preparation of the polyvinyl acetate slurry in Example 1, except that Eudragid E100 was used in place of polyvinyl acetate.

(3) Preparation of Talc Slurry

A talc slurry was prepared by admixing and stirring talc (277.5 g), Emulgen 106 (22.5 g) and water (700 g), followed by dispersion using a sand mill.

(4) Preparation of Methionine Oral Administration Composition 2

Methionine Oral Administration Composition 2 was prepared in the same manner as in Example 1, except that the coating liquid was prepared by suspending the ethyl cellulose emulsion used in Example 1 (270 g), the stearic acid emulsion (60 g), the Eudragid E100 slurry (160 g) and the talc slurry (110 g) in water (300 g) .

EXAMPLE 3

(1) Preparation of Cellulose Acetate Emulsion

Cellulose acetate (acetic acid value: 52%) (200 g), 12 g of sodium lauryl sulfate and 12 g of polyoxyethylene lauryl ether (Emulgen 120 produced by Kao Corp.) were dissolved in acetone (800 g). The solution was added dropwise to water (6 liters) with stirring, and the resulting dispersion was concentrated by removing acetone at 80° C. under reduced pressure (50 torr.) to obtain a cellulose acetate emulsion having a solid content of 30%.

(2) Preparation of Chitosan Slurry

A slurry of chitosan was prepared according to the same method as in the preparation of the AEA slurry in Example 1, except that chitosan was used in place of AEA.

(3) Preparation of Methionine Oral Administration Composition 3

Methionine Oral Administration Composition 3 was prepared in the same manner as in Example 1, except that the coating liquid was prepared by suspending the cellulose acetate emulsion (400 g), the chitosan slurry (160 g) and the polyvinyl acetate slurry obtained in Example 1 (240 g) in water (400 g).

EXAMPLE 4

(1) Preparation of Lysine Granules

Seven hundred grams of a mixture of 6% (w/w) hydroxypropyl cellulose (binder), water and ethanol [water:ethanol=1:1 (v/v)] was added to lysine hydrochloride (2,000 g), and the mixture was kneaded. The resulting mixture was extruded through a cylindrical granulating machine having a screen (diameter: 2.0 mm) and then shaped into spheres by using a Marumerizer. The resulting granules were sieved through a sieve of 8 to 10 mesh, and then dried in a current of air at 60° C. for one hour to obtain granules of a diameter of 1.7 to 2.4 mm.

(2) Preparation of Lysine Oral Administration Composition 4

The ethyl cellulose emulsion used in Example 1 (360 g), the chitosan slurry obtained in Example 3 (120 g) and the polyvinyl acetate slurry obtained in Example 1 (120 g) were suspended in water (300 g), to prepare a coating liquid. By using a fluidized-bed apparatus, the lysine granules (1,000 g) were coated with the coating liquid (900 g) by spraying, to obtain Lysine Oral Administration Composition 4.

EXAMPLE 5

Preparation of Lysine Oral Administration Composition 5

Lysine Oral Administration Composition 5 was prepared in the same manner as in Example 4, except that the coating liquid was prepared by suspending the cellulose acetate emulsion obtained in Example 3 (600 g), the stearic acid emulsion obtained in Example 2 (60 g), the chitosan slurry obtained in Example 3 (120 g) and the talc slurry obtained in Example 2 (60 g) in water (400 g).

EXAMPLE 6

Preparation of Lysine Oral Administration Composition 6

Lysine Oral Administration Composition 6 was prepared in the same manner as in Example 4, except that the coating liquid was prepared by suspending 1,000 g of a mixture of the ethyl cellulose emulsion used in Example 1 (720 g), the AEA slurry obtained in Example 1 (140 g), the polyvinyl acetate slurry obtained in Example 1 (70 g) and the talc slurry obtained in Example 2 (70 g) in 500 g of water.

REFERENCE EXAMPLE 1

Preparation of Methionine Oral Administration Composition (a) Using Solvent

A coating liquid was prepared by dissolving ethyl cellulose (66.7 g), stearic acid (33.3 g), AEA (100 g) and glycerol fatty acid ester (30 g) in 3,000 g of a mixture of isopropanol and acetone [2:1 (v/v)], followed by the addition of 25 g of magnesium stearate as a coagulation inhibitor. By using a fluidized-bed apparatus, the methionine granules used in Example 1 (1,000 g) were coated with the coating liquid (100 g as a solid) by spraying to obtain Methionine Oral Administration Composition (a).

REFERENCE EXAMPLE 2

Preparation of Lysine Oral Administration Composition (b) Using Solvent

A coating liquid was prepared by dissolving ethyl cellulose (83.3 g), stearic acid (16.7 g) and ethanol (50 g) in 3,000 g of a mixture of dichloromethane and ethanol [3:3 (v/v)]. The lysine granules used in Example 4 (1,000 g) were coated with the coating liquid (100 g as a solid) by spraying to obtain Lysine Oral Administration Composition (b).

What is claimed is:

1. A process for producing a composition for ruminants which comprises the steps of:

(a) granulating a polymer, soluble in water at a pH 5.0 or below and insoluble in water at a pH of over 5.0, to fine particles having a diameter of less than 100 μm;

(b) preparing a slurry by dispersing the fine particles obtained in step (a) in water;

(c) preparing a coating material by mixing the slurry obtained in step (b) with an emulsion obtained by forming a solution of a hydrophobic substance selected from the group consisting of saturated fatty acids containing not less than 14 carbon atoms and metal salts thereof, higher fatty alcohols containing not less than 12 carbon atoms, hardened animal oils, hardened vegetable oils, shellac, copolymer resins of styrene, copolymer resins of vinyl chloride, copolymer resins of vinylidene chloride, copolymer resins of acrylic esters, copolymer resins of methacrylic esters, copolymer resins of vinyl acetate, polyesters, polyurethanes, nylons, polyacetals, cellulose acetate, ethyl cellulose and propyl cellulose, in an organic solvent, dispersing the solution in water with an emulsifier and removing the organic solvent by heating; and (d) coating a nucleus containing a physiologically active substance with the coating material obtained in step (c).

\* \* \* \* \*